United States Patent [19]

Wilk

[11] Patent Number: 5,273,026
[45] Date of Patent: Dec. 28, 1993

[54] RETRACTOR AND ASSOCIATED METHOD FOR USE IN LAPAROSCOPIC SURGERY

[76] Inventor: Peter J. Wilk, 185 W. End Ave., New York, N.Y. 10023

[21] Appl. No.: 848,684

[22] Filed: Mar. 6, 1992

[51] Int. Cl.⁵ .............................................. A61B 17/00
[52] U.S. Cl. ................................... 128/20; 606/198; 604/95; 604/107
[58] Field of Search ............... 128/3, 20, 5, 772, 898; 606/191, 198; 604/104, 106–109, 95, 282

[56] References Cited

U.S. PATENT DOCUMENTS

| | | | |
|---|---|---|---|
| 2,067,031 | 1/1937 | Wappler | 606/198 |
| 3,517,128 | 6/1970 | Hines . | |
| 4,198,959 | 4/1980 | Otani | 128/5 |
| 4,224,929 | 9/1980 | Furihata | 128/5 |
| 4,325,387 | 4/1982 | Helfer | 128/772 |
| 4,774,949 | 10/1988 | Fogarty | 128/4 |
| 4,905,667 | 3/1990 | Foerster et al. | 128/4 |
| 4,909,789 | 3/1990 | Taguchi et al. | 604/107 |
| 4,949,706 | 8/1990 | Thon | 128/4 |
| 5,062,847 | 11/1991 | Barnes | 604/107 |
| 5,106,369 | 4/1992 | Christmas | 128/20 X |
| 5,106,381 | 4/1992 | Chikama | 604/95 X |
| 5,108,368 | 4/1992 | Hammerslag et al. | 128/772 |

Primary Examiner—Richard J. Apley
Assistant Examiner—Donna L. Maraglio
Attorney, Agent, or Firm—R. Neil Sudol; Henry D. Coleman

[57] ABSTRACT

A retractor for use in laparoscopic surgery comprises a substantially rigid tubular outer member and a retractor member at least partially inserted in the tubular member for slidable motion in an axial direction relative thereto. The retractor member is provided with a distal end portion having limited flexibility which enables a bending of the distal end portion upon application of a bending force greater than a predetermined threshold. In addition, the distal end portion has a spring bias tending to return the distal end portion to a linear configuration upon relaxation of bending force below the threshold. A camming surface is provided on the tubular member at the distal end thereof for bending the distal end portion during a distally directed longitudinal stroke of the retractor member relative to the tubular member, whereby at least a terminal part of the distal end portion extends at an angle with respect to the tubular member.

18 Claims, 1 Drawing Sheet

RETRACTOR AND ASSOCIATED METHOD FOR USE IN LAPAROSCOPIC SURGERY

BACKGROUND OF THE INVENTION

This invention relates to a surgical instrument. More particularly, this invention relates to a retractor for use in laparoscopic surgery. This invention also relates to an associated surgical method.

In laparoscopic surgery, one or more openings are made in a patient's abdominal wall, usually by piercing the wall with the aid of a trocar. A laparoscope is inserted through one of the openings and, more particularly, through a trocar sleeve or cannula in the opening, to enable a surgeon to see organs and tissues which are located in the patient's abdominal cavity. Usually, operating instruments such as grasping forceps and cutting tools are inserted into the abdominal cavity through trocar sleeves or cannulas in ancillary openings made in the abdominal wall.

Some internal organs or tissues are disposed under other organs when the patient is lying on his or her back (the normal posture during laparoscopic surgery). The overlying organs must be lifted or otherwise displaced prior to operating on the underlying organs. Generally, a grasping forceps is used to grip an overlying organ and pull it upwardly to provide access to the desired surgical site. This procedure is frequently cumbersome, if not ineffective, to adequately expose the underlying organs and tissues.

OBJECTS OF THE INVENTION

An object of the present invention is to provide an improved technique for temporarily displacing an internal body organ of a patient during laparoscopic surgery.

Another object of the present invention is to provide an associated surgical instrument for use in laparoscopic surgery.

Another, more particular, object of the present invention is to provide a laparoscopic surgical retractor which has a capability of assuming different configurations inside the patient's abdomen, to facilitate a retraction operation.

A further particular object of the present invention is to provide such a retractor which is easy to use and inexpensive to fabricate.

SUMMARY OF THE INVENTION

A retractor for use in laparoscopic surgery comprises, in accordance with the present invention, a substantially rigid tubular outer member and a retractor member at least partially inserted in the tubular member for slidable motion in an axial direction relative thereto. The retractor member is provided with a distal end portion having limited flexibility which enables a bending of the distal end portion upon application of a bending force greater than a predetermined threshold. In addition, the distal end portion has a spring bias tending to return the distal end portion to a linear configuration upon relaxation of bending force below the threshold. A flexing structure is provided on the tubular member for bending the distal end portion of the retractor member during a distally directed longitudinal stroke of the retractor member relative to the tubular member, whereby at least a terminal part of the distal end portion extends at an angle with respect to the tubular member.

The flexing structure may include a curved camming surface inside the tubular member at a distal end thereof. An axially directed force applied to the retractor member which pushes the distal end portion of the retractor member against the camming surface causes the distal end portion to bend at the camming surface.

Additionally, the tubular member is provided at a distal end with a lateral opening to enable the outwardly turned terminal part of the distal end portion of the retractor member to project out from the tubular member.

According to another feature of the present invention, flexing components are operatively connected to the retractor member for bending a terminal segment of the distal end portion and for maintaining the terminal segment in a bent configuration in opposition to the spring bias during a laparoscopic surgical procedure. The flexing components may include a cable extending longitudinally along the retractor member and means for applying tension to the cable. The tension may be supplied by motors controlled by an actuator such as a joystick or roller ball mouse. Alternatively, the tension may be supplied manually via a crank or knob which can be held in position by a lock upon the achievement of a desired end configuration of the terminal segment of the retractor member.

In one specific embodiment of the invention, the flexing components include a plurality of cables extending longitudinally along the retractor member and actuators for selectively applying tension to the cables. Thus, the terminal segment of the retractor member may be bent in virtually any direction relative to the outwardly turned part of the distal end portion.

According to another feature of the present invention, the tubular member is provided with a door or other structure for closing the lateral opening upon a retraction of the retractor member back into the tubular member.

A retraction method for use in laparoscopic surgery comprises, in accordance with the present invention, the steps of (a) inserting a tubular member through a trocar sleeve so that a distal end of the tubular member projects into a patient's abdominal cavity and (b) shifting, in a distal direction through the tubular member, an elongate retractor member. The retractor member has a distal end portion with a limited flexibility enabling a bending of the distal end portion upon application of a bending force greater than a predetermined threshold. In addition, the distal end portion of the retractor member has a spring bias tending to return the distal end portion to a linear configuration upon relaxation of bending force below the threshold. In another step (c), a distal end portion of the retractor member is continuously bent during the longitudinal shifting of the retractor member, so that an increasingly long part of the distal end portion extends outwardly at an angle relative to the tubular member. Upon a termination of that longitudinal shifting, a selected internal body organ of the patient is engaged with the part of the retractor member projecting from the tubular member. A force is then exerted on the tubular member and the retractor member to shift the selected internal body organ.

According to a specific feature of the present invention, the bending of the distal end portion of the retractor member includes the step of pushing the distal end portion against a curved camming surface inside the tubular member at a distal end thereof.

In another step of the method, the straight part of the distal end portion is projected out through a lateral opening in the tubular member.

Pursuant to another feature of the present invention, a terminal segment of the distal end portion of the retractor member is bent and maintained in a bent configuration in opposition to the spring bias during a laparoscopic surgical procedure. The bent end segment serves to facilitate the hooking and the retracting of the selected internal organ.

Bending the terminal segment may be implemented by exerting tension on a cable extending longitudinally along the retractor member.

According to another feature of the present invention, the distal end portion of the retractor member is retracted or pulled back into the tubular member and the opening at the distal end of the tubular member is closed upon completing the step of retracting.

The present invention provides an improved technique for temporarily displacing an internal body organ of a patient during laparoscopic surgery. A surgical instrument in accordance with the present invention is an effective laparoscopic retractor and facilitates the temporary displacement of organs which may be difficult to move with a flat or straight retractor member.

DETAILED DESCRIPTION

Figure 1:
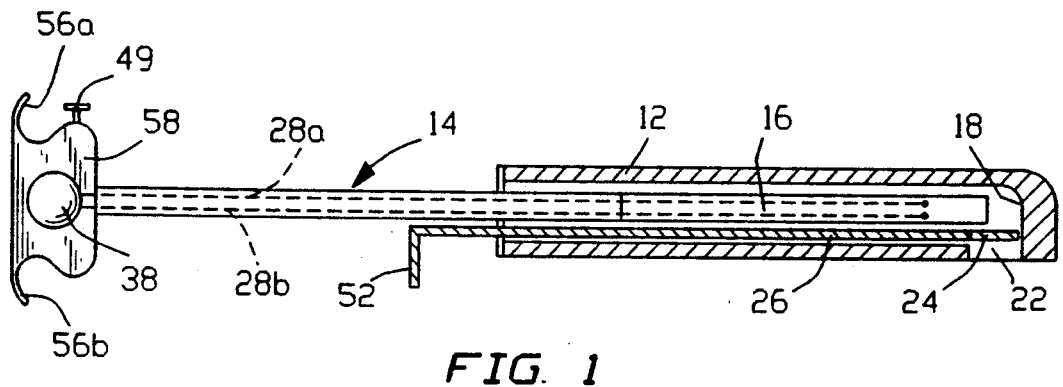
FIG. 1 is a partially a schematic longitudinal cross-sectional view and partially a side elevational view of a retractor in accordance with the present invention, for use in laparoscopic surgery, showing the retractor with a withdrawn retractor member.

As illustrated in FIG. 1, a retractor for use in laparoscopic surgery comprises a substantially rigid tubular outer member 12 and a retractor member 14 partially inserted in tubular member 12 for slidable motion in an axial or longitudinal direction relative thereto. Retractor member 14 is provided with a distal end portion 16 having limited flexibility which enables a bending of the distal end portion upon application of a bending force greater than a predetermined threshold. In addition, distal end portion 16 of retractor member 14 has a spring bias tending to return the distal end portion to a linear configuration upon relaxation of the bending force below the threshold.

A flexing structure in the form of an internal camming surface 18 is provided in tubular member 12, at a distal end thereof, for bending distal end portion 16 of retractor member 14 during a distally directed longitudinal stroke of the retractor member relative to tubular member 12. An axially directed force applied to retractor member 14 which pushes distal end portion 16 thereof against camming surface 18 causes the distal end portion of retractor member 14 to bend at the camming surface. Upon such an extension stroke of retractor member 14, at least a terminal part 20 of distal end portion 16 extends substantially radially, i.e., at an angle with respect to tubular member, as illustrated in FIG. 2.

Figure 2:
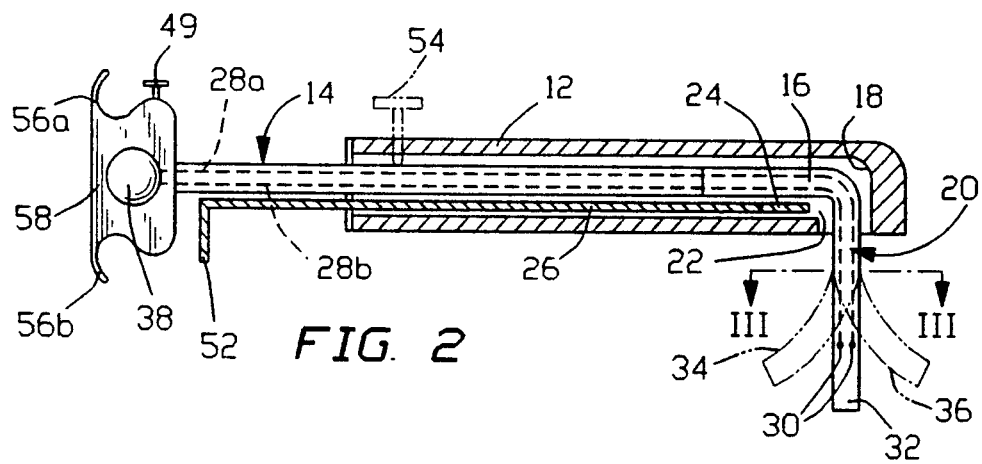
FIG. 2 is a view similar to FIG. 1, showing the retractor member of that drawing figure in an extended, use position.

Additionally, tubular member 12 is provided at its distal end with a lateral opening 22 to enable the outwardly turned terminal part 20 of distal end portion 16 of retractor member 14 to project out from tubular member 12, as shown in FIG. 2.

Tubular member 12 is provided with a door 24 connected to the distal end of a push/pull rod 26 for closing lateral opening 22 upon a retraction of distal end portion 16 of retractor member 14 back into tubular member 12. Generally, as illustrated in FIG. 1, rod 26 and concomitantly door 24 are disposed in a distal position to close opening 22 during an insertion of the distal end of tubular member 12 into a patient's abdominal cavity through a laparoscopic trocar sleeve or cannula (not shown).

Flexing components in the form of cables 28a and 28b are connected to a free end of retractor member 14 at 30 for bending a terminal segment 32 of distal end portion 16 upon an extension thereof due to a distally directed motion of retractor member 14, as shown in FIG. 2. Terminal segment 32 takes on a generally hook shape, as illustrated in phantom lines at 34 and 36 in FIG. 2, upon the selective tensioning of cables 28a and 28b.

At a proximal end, cables 28a and 28b are operatively connected to an actuator member 38. Actuator member 38 may take the form of one or two rotary knobs or cranks for manually exerting tension on cables 28a and 28b to bend terminal segment 32 into hook shape 34 or 36. Alternatively, actuator member 38 may take the form of a mouse type roller ball or joystick 40 illustrated in block form in FIG. 3.

Figure 3:
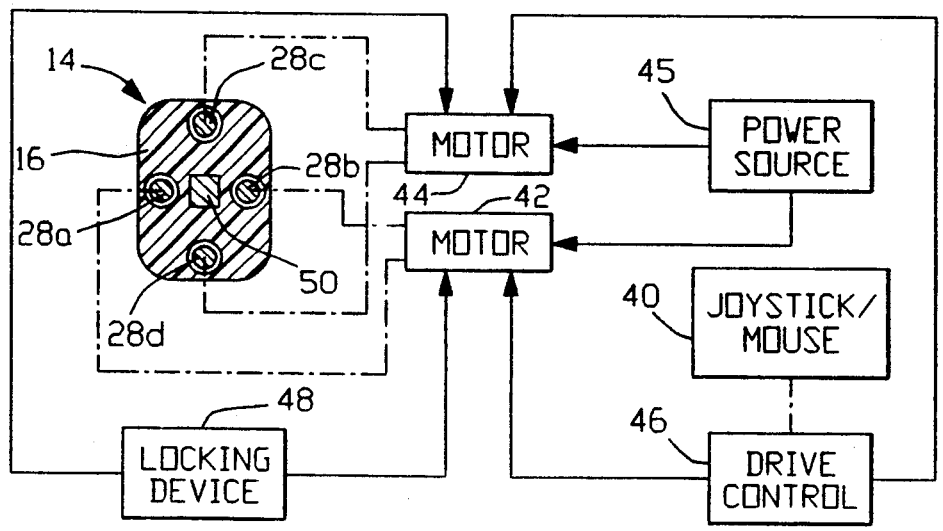
FIG. 3 is partially a transverse cross-sectional view taken along line III—III in FIG. 2 and partially a block diagram of a retractor member control system, in accordance with the present invention.

As illustrated in FIG. 3, cables 28a and 28b may constitute one of two cable pairs 28a, 28b and 28c, 28d for completely controlling the direction in which terminal segment 32 is turned or hooked prior to or during a shifting of an organ inside a patient. In the partially automatic embodiment of FIG. 3, cables 28a and 28b are operatively connected to a first drive motor 42, while cables 38c and 28d are operatively linked to another drive motor 44. Motors 42 and 44 are, in turn, energized by a power source 45 in response to signals from a control unit 46. Control unit 46 is operatively coupled with joystick or mouse actuator 40 for detecting the orientation thereof about two axes (not shown). Control unit 46 may operate like conventional circuitry of a joystick or mouse for controlling the orientation of terminal segment 32.

As further illustrated in FIG. 3, a locking mechanism 48 including an actuator button 49 (FIGS. 1 and 2) is operatively connected to motors 42 and 44 and/or cables 28a, 28b and 28c, 28d for maintaining terminal segment 32 in a bent configuration 34, 36 in opposition to a spring bias exerted by an elongate memory element 50 passing longitudinally through distal end portion 16.

During a laparoscopic surgical procedure, tubular member 12 is inserted through a trocar sleeve (not shown) which traverses a patient's abdominal wall. Upon the insertion of tubular member 12 so that a distal end thereof projects into the patient's abdominal cavity, a finger hook 52 is grasped to pull rod 26 in a proximal direction and thereby shift door 24 to open opening 22. Subsequently, the operating surgeon or an assistant pushes retractor member 14 in a distal direction through tubular member 12 so that distal end portion 16 is bent against camming surface 18 and out through opening 22, whereby retractor member 14 is reconfigured from the linear configuration of FIG. 1 to the L-shaped configuration of FIG. 2.

During the distally directed longitudinal motion of retractor member 14, distal end portion 16 of the retractor member is continuously bent, terminal part 20 becoming increasingly long and extending outwardly at an angle (e.g., 90°) relative to tubular member 12. The outwardly projecting terminal part 20 of retractor member 14 is brought into engagement with a selected internal body organ of a patient (visualized through a laparoscope). A force is exerted on the retractor member 14 and/or tubular member 12 to push or pull the selected internal body organ and thereby effectuate a shifting thereof to facilitate a laparoscopic operation.

A further locking device 54 (FIG. 2) may be provided on tubular member 12 for locking retractor member 14 to tubular member 12 during a retraction operation wherein distal end portion 16 engages an internal body organ of a patient.

Optionally, terminal segment 32 of distal end portion 16 of retractor member 14 is bent into a hook-shaped configuration, e.g., configuration 34 or 36 in FIG. 2, and maintained, e.g., via locking mechanism 48, in that configuration in opposition to the spring bias exerted by memory element 50. The hook shaped configuration given to terminal segment 32 is adapted to maximize an effective displacement of a selected internal body organ.

Upon the completion of the laparoscopic procedure, locking mechanism 48 is deactivated and tension is relaxed on cables 28a, 28b and 28c, 28d. Locking device 54 is released and finger grips 56a and 56b (FIGS. 1 and 2) on a body portion 58 of retractor member 14 are engaged with the fingers and used to draw retractor member 14 back into tubular member 12. Upon the disposition of distal end portion 16 inside tubular member 12, rod 26 is pushed in the distal direction so that door 24 closes opening 22. Tubular member 12 is then withdrawn from the patient's body cavity through the laparoscopic trocar or cannula (not shown).

Although the invention has been described in terms of particular embodiments and applications, one of ordinary skill in the art, in light of this teaching, can generate additional embodiments and modifications without departing from the spirit of or exceeding the scope of the claimed invention. For example, equivalent means such as hydraulic or pneumatic circuits may be used for flexing the terminal segment of the retractor member to produce a hook or an arcuate form for facilitating the retraction of an internal body organ of a patient.

Accordingly, it is to be understood that the drawings and descriptions herein are offered by way of example to facilitate comprehension of the invention and should not be construed to limit the scope thereof.

What is claimed is:

1. A retractor for use in laparoscopic surgery, comprising:
   a substantially rigid tubular outer member;
   a retractor member at least partially inserted in said tubular outer member for slidable motion in an axial direction relative thereto, said retractor member being provided with a distal end portion having limited flexibility enabling a bending of said distal end portion upon application of a bending force greater than a predetermined threshold, said distal end portion having a spring bias tending to return said distal end portion to a linear configuration upon relaxation of bending force below said threshold; and
   flexing means on said tubular outer member for bending said distal end portion during a distally directed longitudinal stroke thereof relative to said tubular outer member, whereby at least a terminal part of said distal end portion extends at an angle with respect to said tubular outer member.

2. The retractor defined in claim 1 wherein said flexing means includes a curved camming surface inside said tubular outer member at a distal end thereof, whereby an axially directed force applied to said retractor member and pushing said distal end portion against said camming surface causes said distal end portion to bend at said camming surface.

3. The retractor defined in claim 2 wherein said tubular outer member is provided at a distal end with a lateral opening to enable an outwardly turned part of said retractor member to project out from said tubular outer member.

4. The retractor defined in claim 3, further comprising additional flexing means operatively connected to said retractor member for bending a terminal segment of said distal end portion and for maintaining said terminal segment in a bent configuration in opposition to said spring bias during a laparoscopic surgical procedure.

5. The retractor defined in claim 4 wherein said additional flexing means includes a cable extending longitudinally along said retractor member and means for applying tension to said cable.

6. The retractor defined in claim 4 wherein said additional flexing means includes a plurality of cables extending longitudinally along said retractor member and means for selectively applying tension to said cables.

7. The retractor defined in claim 3, further comprising means on said tubular outer member for closing said opening upon a retraction of said retractor member back into said tubular outer member.

8. The retractor defined in claim 1, further comprising additional flexing means operatively connected to said retractor member for bending a terminal segment thereof and for maintaining said terminal segment in a bent configuration in opposition to said spring bias during a laparoscopic surgical procedure.

9. The retractor defined in claim 8 wherein said additional flexing means includes a cable extending longitudinally along said retractor member and means for applying tension to said cable.

10. The retractor defined in claim 8 wherein said additional flexing means includes a plurality of cables extending longitudinally along said retractor member and means for selectively applying tension to said cables.

11. A retraction method for use in laparoscopic surgery, comprising the steps of:
   providing a trocar sleeve;
   disposing said trocar sleeve in an abdominal wall of a patient;
   providing a rigid tubular member longitudinally traversed by an elongate retractor member having a distal end portion with a limited flexibility enabling a bending of said distal end portion upon application of a bending force greater than a predetermined threshold, said distal end portion having a spring bias tending to return said distal end portion to a linear configuration upon relaxation of bending force below said threshold;
   inserting said tubular member through said trocar sleeve so that a distal end of the tubular member projects into an abdominal cavity of the patient;

shifting, in a distal direction through said tubular member, said elongate retractor member;

continuously bending said distal end portion of said retractor member during said step of shifting so that an increasingly long part of said distal end portion extends outwardly at an angle relative to said tubular member;

upon a termination of said step of shifting; engaging a selected internal body organ of the patient with the part of the retractor member projecting from said tubular member; and upon engaging the selected internal body organ with said retractor member, exerting a force on said tubular member and said retractor member to shift said selected internal body organ.

12. The method defined in claim 11 wherein said tubular member is provided at a distal end with a curved camming surface, said step of bending including the step of pushing said distal end portion against said curved camming surface.

13. The method defined in claim 12 wherein said tubular member is provided at its distal end with a lateral opening, further comprising the step of moving said part of said distal end portion out through said lateral opening in said tubular member.

14. The method defined in claim 13, further comprising the steps of bending a terminal segment of said distal end portion and maintaining said terminal segment in a bent configuration in opposition to said spring bias during a laparoscopic surgical procedure.

15. The method defined in claim 14 wherein said retractor member is a tension-controlled retractor member including longitudinally extending cables, said step of bending said terminal segment including the step of exerting tension on one of said cables.

16. The method defined in claim 13 wherein said tubular member is provided with a slidable rod for closing and opening said lateral opening, further comprising the steps of retracting said distal end portion back into said tubular member and sliding said rod to close said opening upon completing said step of retracting.

17. The method defined in claim 11, further comprising the steps of bending a terminal segment of said distal end portion and maintaining said terminal segment in a bent configuration in opposition to said spring bias during a laparoscopic surgical procedure.

18. The method defined in claim 17 wherein said retractor member is a tension-controlled retractor member including longitudinally extending cables, said step of bending said terminal segment includes the step of exerting tension on one of said cables.

* * * * *